(12) United States Patent
Elyasaf et al.

(10) Patent No.: US 7,504,622 B2
(45) Date of Patent: Mar. 17, 2009

(54) HIGH THROUGHPUT MULTI BEAM DETECTION SYSTEM AND METHOD

(75) Inventors: Emanuel Elyasaf, Rehovot (IL); Nissim Elmaliah, Raanana (IL)

(73) Assignee: Applied Materials, Israel, Ltd., Rehovot (IL)

( * ) Notice: Subject to any disclaimer, the term of this patent is extended or adjusted under 35 U.S.C. 154(b) by 190 days.

(21) Appl. No.: 11/684,965

(22) Filed: Mar. 12, 2007

(65) Prior Publication Data

US 2007/0228274 A1 Oct. 4, 2007

Related U.S. Application Data

(60) Provisional application No. 60/744,159, filed on Apr. 3, 2006.

(51) Int. Cl.
*G02B 6/04* (2006.01)
*G01N 23/00* (2006.01)
*H04B 10/00* (2006.01)

(52) U.S. Cl. .................. 250/306; 250/307; 385/115; 385/116; 385/88; 385/89; 398/151; 398/156

(58) Field of Classification Search .............. 250/306, 250/307; 385/115, 116, 88, 89; 398/151, 398/156

See application file for complete search history.

(56) References Cited

U.S. PATENT DOCUMENTS 7,269,321 B2 * 9/2007 Morris et al. .............. 385/115

2006/0034613 A1 * 2/2006 Morris et al. .............. 398/142

* cited by examiner

*Primary Examiner*—Nikita Wells
(74) *Attorney, Agent, or Firm*—Tarek N. Fahmi

(57) ABSTRACT

A high-throughput inspection system and method. The system includes: (i) a charged particles to light converter adapted to convert a secondary array of charged particle beams to a first array of light beams; wherein the first array of light beams is characterized by a first ratio of an average first array light beam diameter to an average distance between adjacent first array light beams of the first array; (ii) first optics, positioned between the charged particles to light converter and between inputs of multiple fibers, wherein the first optics is adapted to provide a second array of light beams; wherein each second array light beam corresponds to a first array light beam; wherein the second array of light beams is characterized by a second ratio of an average second array light beam diameter to an average distance between adjacent second array light beams; wherein the second ratio is substantially smaller than the first ratio; (iii) multiple fibers that are adapted to direct second array light beams towards multiple detectors; wherein the inputs of the multiple fibers are positioned in response to an expected spatial disorder of the second array of light beams and to diameters of second array light beams; and (iv) multiple detectors, adapted to detect light from the multiple fibers.

20 Claims, 3 Drawing Sheets converting a secondary array of charged particle beams to a first array of light beams. The first array of light beams is characterized by a first ratio of an average first array light beam diameter to an average distance between adjacent first array light beams of the first array. 310 optically converting the first array of light beams to a second array of light beams directed onto multiple inputs of multiple fibers. Each second array light beam corresponds to a first array light beam. The second array of light beams is characterized by a second ratio of an average second array light beam diameter to an average distance between adjacent second array light beams. The second ratio is substantially smaller than the first ratio 320 magnifying the first array of light beams to provide a magnified array of light beams 322 reducing a size of magnified array light beams without substantially affecting a distance between adjacent light beams. 324 directing, by the multiple fibers, the second array light beams towards multiple detectors. The inputs of the multiple fibers are positioned in response to an expected spatial disorder of the second array of light beams and to diameters of second array light beams. 330 imaging, by multiple micro-lens arrays, an image formed at outputs of the multiple fibers onto multiple detectors. 332 detecting light from the multiple fibers by the multiple detectors. 340 outputting multiple detection signals from multiple detectors via a large number of data paths. 350

HIGH THROUGHPUT MULTI BEAM DETECTION SYSTEM AND METHOD

RELATED APPLICATIONS

This application claims the priority of U.S. provisional patent Ser. No. 60/744,159, filing date Apr. 3, 2006.

FIELD OF THE INVENTION

The present invention relates to high throughput inspection systems and methods, especially for inspection or metrology of integrated circuits.

BACKGROUND

Optical inspection systems inspect a wafer by illuminating the wafer's surface, collecting light that is scattered or reflected from the wafer's surface, and detecting the scattered or reflected light by light detectors.

The illumination can involve scanning the wafer's surface by a single light beam, by multiple-light beam and even by area illumination. The light detectors (also referred to as light sensors) can include discrete detectors as well as detector arrays.

There is a greater emphasis on the throughput of inspection devices and accordingly on the throughput of scanners, as the design rules for semiconductors rapidly shrink without a corresponding decrease of the inspection sequence time period or the overall size of semiconductor dies or wafers.

The throughput of optical inspection systems were increased by using area illumination or multiple beam illumination. U.S. Pat. No. 6,671,042 of Almogy, U.S. Pat. No. 6,639,201 of Almogy et al., U.S. Pat. Nos. 6,578,961 and 6,208,411 of Vaez-Iravani and U.S. Pat. No. 6,248,988 of Krantz, which are incorporated herein by reference, describe state of the art inspection systems.

There is a need to further increase the throughput of optical inspection systems, and especially cost effective optical inspection systems.

SUMMARY OF THE INVENTION

A high-throughput inspection system. The system includes: (i) a charged particles to light converter adapted to convert a secondary array of charged particle beams to a first array of light beams; wherein the first array of light beams is characterized by a first ratio of an average first array light beam diameter to an average distance between adjacent first array light beams of the first array; (ii) first optics, positioned between the charged particles to light converter and between inputs of multiple fibers, wherein the first optics is adapted to provide a second array of light beams; wherein each second array light beam corresponds to a first array light beam; wherein the second array of light beams is characterized by a second ratio of an average second array light beam diameter to an average distance between adjacent second array light beams; wherein the second ratio is substantially smaller than the first ratio; (iii) multiple fibers that are adapted to direct second array light beams towards multiple detectors; wherein the inputs of the multiple fibers are positioned in response to an expected spatial disorder of the second array of light beams and to diameters of second array light beams; and (iv) multiple detectors, adapted to detect light from the multiple fibers.

A high-throughput inspection method, the method includes: converting a secondary array of charged particle beams to a first array of light beams; wherein the first array of light beams is characterized by a first ratio of an average first array light beam diameter to an average distance between adjacent first array light beams of the first array; optically converting the first array of light beams to a second array of light beams directed onto multiple inputs of multiple fibers; wherein each second array light beam corresponds to a first array light beam; wherein the second array of light beams is characterized by a second ratio of an average second array light beam diameter to an average distance between adjacent second array light beams; wherein the second ratio is substantially smaller than the first ratio; directing, by the multiple fibers, the second array light beams towards multiple detectors; wherein the inputs of the multiple fibers are positioned in response to an expected spatial disorder of the second array of light beams and to diameters of second array light beams; and detecting light from the multiple fibers by the multiple detectors.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which:

FIG. 3 illustrates a high throughput inspection method, according to an embodiment of the invention.

DETAILED DESCRIPTION OF THE PREDEFINED EMBODIMENTS

Reference will now be made in greater detail to exemplary embodiments of the present invention. In the following description made in conjunction with the exemplary embodiments of the present invention, a variety of specific elements are described. The following detailed description is of exemplary embodiments of the invention but the invention is not limited thereto, as modifications and supplemental structures may be added, as would be apparent to those skilled in the art. Also, in the following description of the present invention, a detailed description of known functions and configurations incorporated herein is omitted.

According to an embodiment of the invention a system is provided. The high throughput of the system is achieved by illuminating an inspected object by an array of primary charged particle beams (such as electron beams) that includes a very large number (typically from some hundreds to some thousands) of charged particle beams, collecting an array of secondary charged particle beams, performing an charged particle to optic conversion to provide a first array of light beams (that includes a very large number of first array light beams), and providing a very large number of light beams to a very large number of detectors, after passing through a first optics and through multiple fibers. It is noted that due to mechanical constrains and due to the need to provide a very high data rate system there is a need to use a large number of spaced apart detectors.

Conveniently, in order to reduce and even eliminate light energy losses and cross-talk resulting from the propagation of the multiple light beams towards the multiple detectors, the fibers are positioned such as to receive most (if not almost all) of the light energy of the first array light beams.

Figure 1:
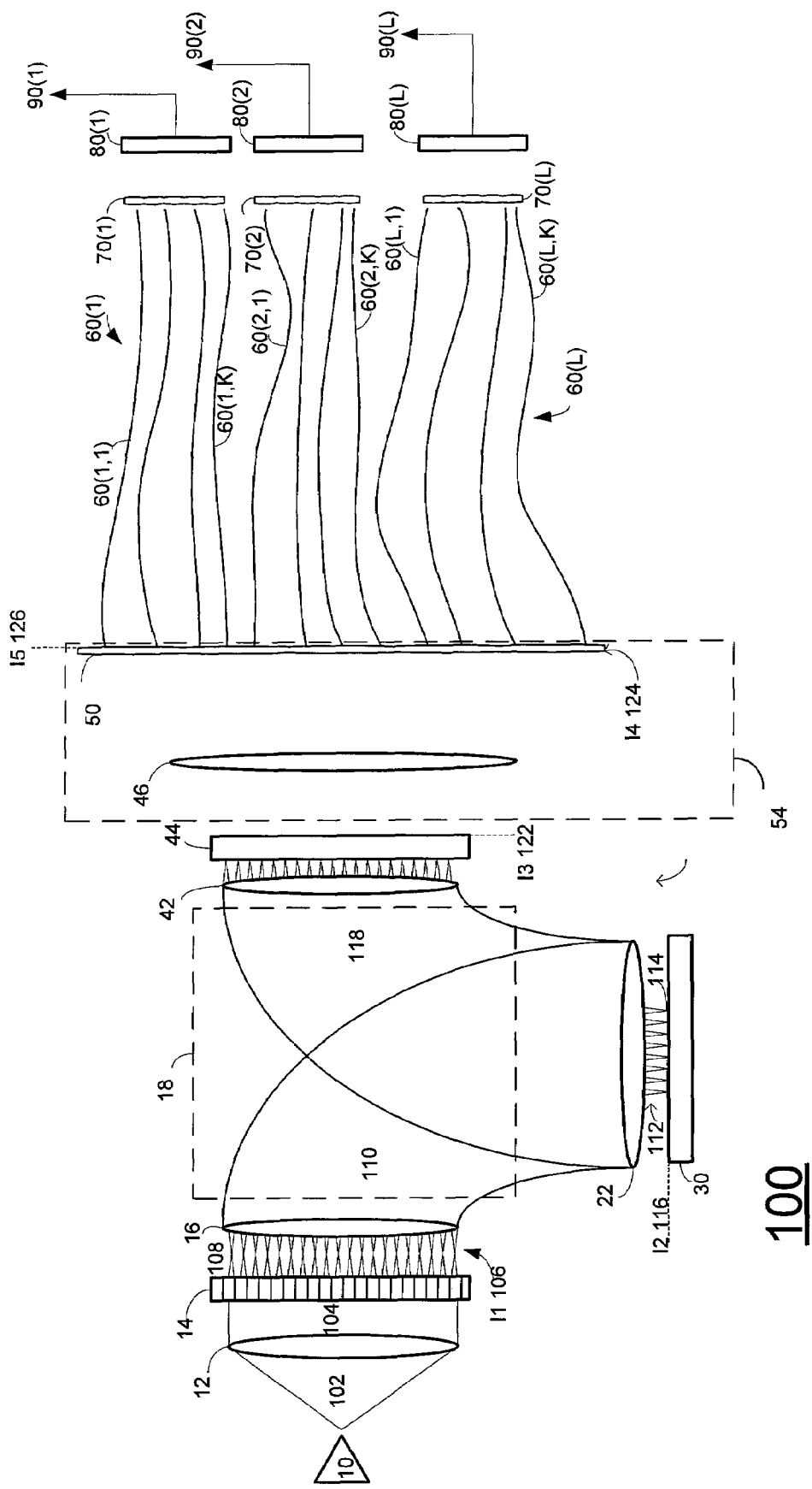
FIG. 1 illustrates an exemplary embodiment of a high throughput inspection system, according to an embodiment of the invention.

In order to use commercially available detectors and in order to impose reasonable positioning constraints on the fibers, the first optics alters the relationship between light beam diameters and the distance between adjacent light beams. This may involve providing second array light beams that are smaller than the input aperture of a fiber but are relatively spaced apart from each other, such that relatively coarse positioning of the fibers can guarantee that each fiber receives light (substantially) only from a single light beam. FIG. 1 illustrates system 100 according to an embodiment of the invention.

It is noted that the illustrated system and method can perform metrology and, additionally or alternatively perform inspection, review and the like. For simplicity of explanation it is assumed that the system and method utilized electron beams but other charged particle beams can be used.

System 100 includes: electron source arrangement 10, collimating lens 12, multi-aperture plate 14, first imaging lens 16, beam directing element 18, objective lens 22, second imaging lens 42, scintillator 44, first optics 54, fibers 60(1,1)-60(L,K), micro-lens arrays 70(1)-70(L), and detectors groups 80(1)-80(L). First optics 54 includes first optics micro lens array 50 and magnifying lens 46.

Electron source arrangement 10 generates a diverging beam 102 which is collimated by collimating lens 12 to form a substantially collimated electron beam 104. This beam illuminates a multiple-aperture plate 14. Multiple aperture plate 14 can have various alternative configurations. It is assumed that it forms a staggered array that includes 10,000 apertures. Collimated electron beam 104 passes through multiple aperture plate 14 to provide 10000 primary electron beams. Multiple aperture plate 14 further focuses each of these primary electron beams at a first plane, to provide an intermediate image (I1 108) at focal points 108. First imaging lens 16 and objective lens 22 images the intermediate image onto article 30. First imaging lens 16 and objective lens 22 are oriented in respect to each other, for example by ninety degrees, in order to separate a primary beams path from a secondary beams path. In other words, primary electron beams 110 that pass through first imaging lens 16 propagate at a complex path till they pass through objective lens 22 that in turn focuses them onto object 30. The path is "bent" using electromagnetic components, in a manner known in the art. For example, the primary electron beams can first pass through a homogenous magnetic field deflecting the primary electron beams by a certain angle to the left. They can than pass a drift region that is free of magnetic fields. They then can pass through another homogenous magnetic field that deflects the primary electron beams by another angle such as to enter the objective lens 22 in about ninety degrees to objective lens 22.

Secondary electron form a secondary image (I2 116) on the surface of inspected object 30 that is then imaged (by objective lens 22 and second imaging lens 42) onto scintillator 44, as illustrated by third image (I3) formed on the surface of scintillator 44. Second imaging lens 42 and objective lens 22 are oriented in respect to each other, for example by ninety degrees. In other words, secondary electron beams 118 that pass through objective lens 22 propagate at a complex path till they pass through second imaging lens 42 that in turn focuses them onto scintillator 44. The path is "bent" using electromagnetic components, in a manner known in the art.

The focusing (of primary electron beams) operation and the collection operation (of secondary electron beams) of objective lens 22 are illustrated by multiple rectangulars 112 that end at spots 114 formed on the surface of object 30.

According to an embodiment of the invention the primary and the secondary electron beams are arranged such as to form a rectangular array. According to another embodiment the light beams are arranged such as to form a staggered (or graded) array in which even rows and odd rows are misaligned by a predefined distance. For convenience of explanation only the latter formation is illustrated. It is noted that the array can be symmetrical, partially symmetrical and the like.

Second imaging lens 42 focuses (as illustrated by multiple rectangulars 120) multiple secondary primary beams 118 onto scintillator 44 to form a third image (I3 122) that is also referred to as first array of light beams 122.

First array of light beams 122 is characterized by a first ratio of an average first array light beam diameter to an average distance between adjacent first array light beams of the first array. Typically, the diameter of first light beams is of about the same magnitude as the distance between adjacent first array light beams. It is noted that different first array light beams can have different diameters and that they first array of light beams does not necessarily include evenly spaced first array light beam.

The first array light beams are relatively close to each other, thus they can not be merely detected by detectors are placed in proximate to each other, and near scintillator 44 due to mechanical constraints.

The inventors used a first array of light beams that included 10000 first array light beams, the diameter of a typical first array light beam was about 150 microns and the distance between adjacent first array light beams was about 200 microns. Due to the very large amount of first array light beams and the small distance between adjacent first array light beams detections and even light guides such as fibers can not simply be located near scintillator 44.

In order to space apart the light beams without substantially magnifying the diameter of the light beams first optics 54 was placed between scintillator 44 and the inputs of multiple fiber optics (also referred to as fibers) 60(1,1)-60(L,K).

First optics 54 converts first array of light beams 122 to provide second array of light beams 126 that form fourth image I4 126 at an imaginary plane that includes the locations of the inputs of fibers 60(1,1)-60(L,K).

The inputs of the multiple fibers are positioned in response to an expected spatial disorder of the second array of light beams and to diameters of second array light beams. Especially, the inputs of the multiple fibers are positioned such as to collect substantially the whole light energy of the second array light beams, regardless of their current spatial displacement.

It is noted that each second array light beam corresponds to a first array light beam. Second array of light beams 126 is characterized by a second ratio of an average second array light beam diameter to an average distance between adjacent second array light beams. The second ratio is substantially smaller than the first ratio. Conveniently, the first ratio is at least five times bigger than the second ratio.

Multiple fibers 60(1,1)-60(L,K) are adapted to direct second array light beams towards multiple detectors 80 that are adapted to detect light from the multiple fibers.

Conveniently, first optics 54 includes magnifying lens 46 that is followed by first optics micro-lens array 50.

The micro-lenses of first optics micro-lens array 50 are conveniently positioned in response to an expected spatial disorder of the first array of light beams and to a magnification of the magnifying lens. Especially, the micro-lenses of first optics micro-lens array 50 are positioned such as to collect substantially the whole light energy of the first array light beams (after passing through magnifying lens 50), regardless of their current spatial displacement.

Conveniently, fiber plate 62 that includes multiple apertures (holes) is connected to fibers 60(1,1)-60(M,K). The locations of these holes are responsive to the expected location of the second array light beams.

Conveniently, first optics micro-lens array 50 and fiber plate 62 are aligned and assembled together. The precise alignment between these two components assists in the conservation of the illumination energy along the optical path.

Conveniently, the fibers are grouped into multiple groups of fibers such as groups 60(1)-60(M). Each group of fibers directs light to a corresponding group of detectors out of groups of detectors 80(1)-80(M). Each group of detectors includes multiple (conveniently discrete) light detectors that are arranged in a one dimensional or a two dimensional formation. Conveniently two rows of sixteen detectors each can be included in a single group of detectors.

Conveniently, in order to provide a very high throughput, the detectors are connected in parallel data paths to one or more storage units and/or to one or more image processors. A data path can be allocated per each detector or to a small set of detectors. A data path of a discrete detector usually include a single line, but this is not necessarily so. The data paths can be arranged in groups such as data path groups 90(1)-90(L). It is noted that various buffering and multiplexing techniques can be applied for retrieving the detection signals from the detectors.

According to an embodiment of the invention each group of fibers is followed by a micro-lens array (such as micro-lens arrays 70(1)-70(M)), wherein each micro-lens array (such as 70(m)) is positioned between a group of fiber bundles (60(m)) and a group of detectors (80(m)). Conveniently, the groups of detectors are spaced apart from each other.

Conveniently, by micro-lenses of first optics micro-lens array 50 and the inputs of fibers 60 are positioned such as to substantially eliminate optical energy losses resulting from a propagation of light from the charged particles to light converter to the multiple sensors.

Conveniently, the detectors are discrete detectors (not array detectors) such as avalanche photo diodes detectors. The group of detectors may include multiple discrete detectors that are grouped together. It is noted that the data can be serially read from each detector or from a group or sub-group of detectors in a serial manner.

Conveniently, system 100 is adapted to operate at very high data rates that may exceed 10 mega pixels per sensor. These very high data rates can be obtained by retrieving detection signals in parallel from one or few detectors.

Conveniently, scintillator 44 includes a reflective layer that reflects light that is directed towards the beam shaping unit 18. Thus, substantially the whole light energy resulting from the electro-optical conversion of scintillator 44 is directed towards first optics 54.

Conveniently, first optics 54, fibers 60 and multiple micro-lens arrays 70 keep the optical invariant. Since the spots 114 at the surface of object 30 are large and the scintillator 44 emits light over a large angular range, the active area of a sensor should be relatively large.

Fibers can be tailored to fit such light beams, especially in view of the relatively large distance between adjacent second array light beams.

Conveniently, system 100 includes avalanche photo diodes that provide relatively large active area size, a very short decay time, low noise, inter-detector uniformity, low crosstalk and to low cost.

The following example will illustrate an exemplary configuration of system 100.

Primary array of electron beams 110 includes 100×100 primary electron beams. They are focused onto the surface of object 30 to provide one thousand spots 114, the diameter of each spot is about 150 micron and the distance between adjacent spots is about 200 micron. The overall size of this array is about 20×20 mm$^2$.

Scintillator 44 provides first array of light beams 13 122 that includes 100×100 first array light beams that are spaced apart from each other by about (due to distortions) 2 micron, and the diameter of a first array light beam is about 150 microns. The size of the first array of light beams 122 is about 20×20 mm$^2$.

First array of light beams 122 is magnified by first optics magnification lens 46 by a magnification factor of 5 to form third image 124 of about 100×100 mm$^2$. The distance between adjacent light beams is about 1000 microns. The diameter of a light beam is about 750 microns. Conveniently, magnifying lens 46 has a Numerical Aperture (NA) of 0.5 or higher. The space between magnifying lens 46 and scintillator 44 can be filled with a fluid that is characterized by an immersion index of about n=1.83.

First optics micro-lens array 50 reduced the diameter of the light beams without substantially affecting the distance between adjacent light beams. Assuming that first optics micro-lens array 50 has a magnification factor of ⅓ then the diameter of a second array light beam is about 250 microns while the distance between adjacent second array light beams is about 1000 microns.

System 100 can perform various distortion correction steps. For example, the shape of the multiple aperture plate 14 can be shaped such as to compensate (or at least substantially compensate) for distortions introduced by any one (or a combination thereof) of components such as collimating lens 12, first imaging lens 16, beam directing element 18 and/or objective lens 22. Methods for compensating for distortions and multi-aperture plates having distortion correction capabilities are illustrated in PCT patent application international publication serial number WO2005/024881A2.

Nevertheless, even when distortion correction stages are applied, system 100 still distorts the electron and/or light beam arrays.

In order to substantially prevent energy losses the inputs of fibers 60 as well as the micro-lenses of first optics micro-lens array 50 are located such that substantially the whole light beam (even is it is distorted) passes through the appropriate micro-lens and fiber, regardless of the actual distortion of that light beam.

Figure 2:
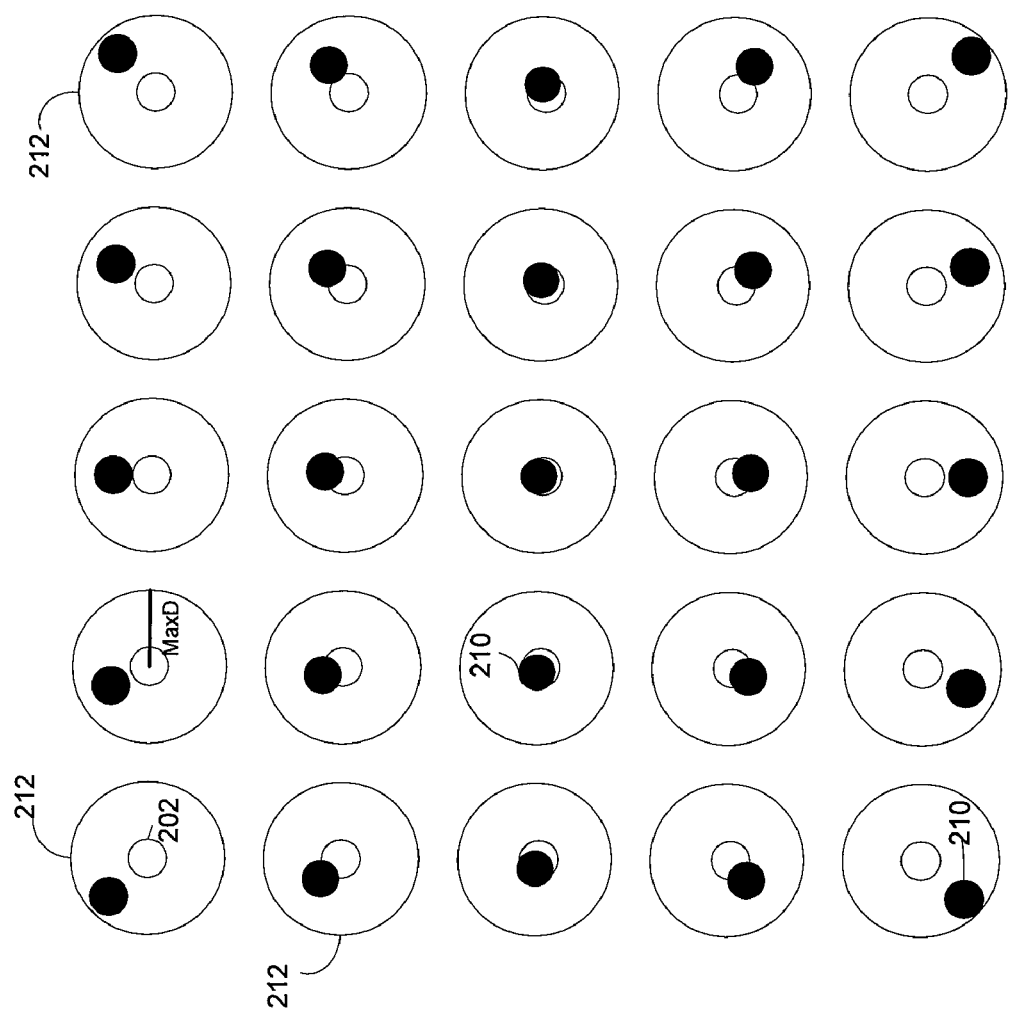
FIG. 2 illustrates a simulated distortion map, according to an embodiment of the invention.

FIG. 2 illustrates simulated distortion map 200, according to an embodiment of the invention.

It is noted that simulated distortion map 200 is out of scale. For example, the spacing between undistorted light beams is about several millimeters while the distortion is in the range of microns. It is further noted that simulated distortion map 200 includes only 5×5 spots, for clarity of explanation.

As can be seen by simulated distortion map 200 an ideally regular array (that can illustrated by points 202) is distorted by system 100 (or some of its components) to provide a distorted array (illustrated by points 210).

It is known that each beam of the ideally regular array can be distorted by a maximal distortion (MaxD). This maximal distortion can be usually being calculated in response to the optical characteristics of the components of system 100, including their aberrations, their distortions, and the like.

The maximal distortion defines a possible light beam location area for each light beam, as illustrated by circles 212 that surround points 210. If a light beam is within the possible light beam location area it will pass through the appropriate micro-lens of first optics micro-lens array 50 and will propagate (without substantial energy loss) through the appropriate fiber.

FIG. 3 is a flow chart of high-throughput inspection method 300 according to an embodiment of the invention.

Method 300 starts by stage 310 of converting a secondary array of charged particle beams to a first array of light beams. The first array of light beams is characterized by a first ratio of an average first array light beam diameter to an average distance between adjacent first array light beams of the first array.

Conveniently, stage 310 involves performing an electro-optical conversion and reflecting light initially directed towards charge particle optics that provided the secondary array of charged particles.

Stage 310 is followed by stage 320 of optically converting the first array of light beams to a second array of light beams directed onto multiple inputs of multiple fibers. Each second array light beam corresponds to a first array light beam. The second array of light beams is characterized by a second ratio of an average second array light beam diameter to an average distance between adjacent second array light beams. The second ratio is substantially smaller than the first ratio. Referring to the example set fourth in previous figures first optics 54 can perform this conversion.

Conveniently, stage 320 includes stage 322 of magnifying the first array of light beams to provide a magnified array of light means and stage 324 of reducing a size of magnified array light beams without substantially affecting a distance between adjacent light beams.

Conveniently, stage 324 includes passing magnified array light beams through a first optics micro-lens array that includes micro-lenses that are positioned in response to an expected spatial disorder of the magnified array light beams. Conveniently, the micro-lens are positioned such as that regardless of the actual distortion of the light beams substantially the whole beam passes through the appropriate micro-lens.

Stage 320 is followed by stage 330 of directing, by the multiple fibers, the second array light beams towards multiple detectors. The inputs of the multiple fibers are positioned in response to an expected spatial disorder of the second array of light beams and to diameters of second array light beams. Referring to the example set fourth in previous figures fibers 60 can direct the second array light beams towards multiple detectors 80.

Conveniently, stage 330 includes stage 332 of imaging, by multiple micro-lens arrays, an image formed at outputs of the multiple fibers onto multiple detectors. Referring to the example set fourth in previous figures the imaging is performed by multiple micro-lenses arrays 70(1)-70(L) positioned between groups of fibers 60(1)-60(L) and groups of detectors 80(1)-80(L).

Conveniently, stage 330 includes directing by multiple groups of fibers, second array light beams towards multiple spaced apart groups of detectors.

Conveniently, the first ratio is at least five times bigger than the second ratio.

Stage 330 is followed by stage 340 of detecting light from the multiple fibers by the multiple detectors. Referring to the example set fourth in previous figures the detection is performed by multiple detectors 80 that can be arranged in spaced apart detector groups such as detector groups 80(1)-80(L).

Conveniently, stage 340 includes detecting at least ten thousand light beams by multiple avalanche photo diodes detectors.

Conveniently, stage 310 involves using a charged particles to light converter, stage 320 includes passing the first array light beam through first optics. The multiple fibers and the first optic are positioned such as to substantially eliminate optical energy losses resulting from a propagation of light from the charged particles to light converter to the multiple sensors.

Conveniently, stage 340 is followed by stage 350 of outputting multiple detection signals from multiple detectors via a large number of data paths.

While this invention has been described in connection with what is presently considered to be the most practical and preferred embodiment, it is to be understood that the invention is not limited to the disclosed embodiment. Rather, it is intended to cover various modifications within the spirit and scope of the appended claims.

What is claimed is:

1. A high-throughput inspection system, comprising:
    a charged particles to light converter adapted to convert a secondary array of charged particle beams to a first array of light beams; wherein the first array of light beams is characterized by a first ratio of an average first array light beam diameter to an average distance between adjacent first array light beams of the first array;
    first optics, positioned between the charged particles to light converter and between inputs of multiple fibers, wherein the first optics is adapted to provide a second array of light beams; wherein each second array light beam corresponds to a first array light beam; wherein the second array of light beams is characterized by a second ratio of an average second array light beam diameter to an average distance between adjacent second array light beams; wherein the second ratio is substantially smaller than the first ratio;
    multiple fibers that are adapted to direct second array light beams towards multiple detectors; wherein the inputs of the multiple fibers are positioned in response to an expected spatial disorder of the second array of light beams and to diameters of second array light beams; and
    multiple detectors, adapted to detect light from the multiple fibers.

2. The system of claim 1 wherein the first optics comprises a magnifying lens adapted to provide a magnified array of light beams; wherein the magnifying lens is followed by a first optics micro-lens array.

3. The system according to claim 2 wherein micro-lenses of the first optics micro-lens arrays are positioned in response to an expected spatial disorder of magnified array light beams.

4. The system according to claim 1 further comprising multiple micro-lens arrays, each micro-lens array positioned between a group of fiber bundles and a group of detectors.

5. The system according to claim 1 wherein the multiple detectors are arranged in spaced apart groups and wherein each group of fibers directs a group of light beams towards a group of detectors.

6. The system according to claim 1 wherein the multiple fibers and the first optics are positioned such as to substantially eliminate optical energy losses resulting from a propagation of light from the charged particles to light converter to the multiple sensors.

7. The system according to claim 1 wherein the first ratio is at least five times bigger than the second ratio.

8. The system according to claim 1 wherein the first array of light beams comprises at least one hundred first array light beams and wherein the multiple detectors comprise avalanche photo diodes detectors.

9. The system according to claim 1 wherein the charged particles to light converter is a scintillator that is adapted to reflect light initially directed towards charge particle optics that provided the secondary array of charged particles.

10. The system according to claim 1 wherein the multiple detectors output detection signals via a large number of data paths.

11. A high-throughput inspection method, the method comprises:
    converting a secondary array of charged particle beams to a first array of light beams;
    wherein the first array of light beams is characterized by a first ratio of an average first array light beam diameter to an average distance between adjacent first array light beams of the first array;
    optically converting the first array of light beams to a second array of light beams directed onto multiple inputs of multiple fibers; wherein each second array light beam corresponds to a first array light beam; wherein the second array of light beams is characterized by a second ratio of an average second array light beam diameter to an average distance between adjacent second array light beams; wherein the second ratio is substantially smaller than the first ratio;
    directing, by the multiple fibers, the second array light beams towards multiple detectors;
    wherein the inputs of the multiple fibers are positioned in response to an expected spatial disorder of the second array of light beams and to diameters of second array light beams; and
    detecting light from the multiple fibers by the multiple detectors.

12. The method of claim 11 wherein the converting comprises magnifying the first array of light beams to provide a magnified array of light means and then reducing a size of magnified array light beams without substantially affecting a distance between adjacent light beams.

13. The method according to claim 12 wherein the stage of reducing a size of magnified array light beams without substantially affecting a distance between adjacent light beams comprises passing magnified array light beams through a first optics micro-lens array that comprises micro-lenses that are positioned in response to an expected spatial disorder of the magnified array light beams.

14. The method according to claim 11 further comprising imaging, by multiple micro-lens arrays, an image formed at outputs of the multiple fibers onto multiple detectors.

15. The method according to claim 11 wherein the directing, by the multiple fibers, second array light beams towards multiple detectors, comprises directing by multiple groups of fibers, second array light beams towards multiple spaced apart groups of detectors.

16. The method according to claim 11 wherein the first ratio is at least five times bigger than the second ratio.

17. The method according to claim 11 wherein the detecting comprises detecting at least ten thousand light beams by multiple avalanche photo diodes detectors.

18. The method according to claim 11 wherein the converting a secondary array of charged particle beams to a first array of light beams comprises performing an electro-optical conversion and reflecting light initially directed towards charge particle optics that provided the secondary array of charged particles.

19. The method according to claim 11 wherein the stage of converting a secondary array of charged particle beams involves using a charged particles to light converter; wherein the stage of optically converting comprises passing the first array light beam through first optics; and wherein the multiple fibers and the first optic are positioned such as to substantially eliminate optical energy losses resulting from a propagation of light from the charged particles to light converter to the multiple sensors.

20. The method according to claim 11 further comprising outputting multiple detection signals from multiple detectors via a large number of data paths.

* * * * *